United States Patent
Beerten et al.

(10) Patent No.: US 10,463,836 B2
(45) Date of Patent: Nov. 5, 2019

(54) SHOWER PATCH BARRIER DEVICES

(71) Applicant: BEDAL NV, Diepenbeek (BE)

(72) Inventors: Falk Beerten, Kontich (BE); David De Munter, Brasschaat (BE); Alexander Van Damme, Bornem (BE)

(73) Assignee: Bedal NV, Diepenbeek (BE)

( * ) Notice: Subject to any disclaimer, the term of this patent is extended or adjusted under 35 U.S.C. 154(b) by 259 days.

(21) Appl. No.: 15/180,450

(22) Filed: Jun. 13, 2016

(65) Prior Publication Data

US 2016/0296727 A1 Oct. 13, 2016

Related U.S. Application Data

(63) Continuation-in-part of application No. PCT/EP2014/077214, filed on Dec. 10, 2014.

(30) Foreign Application Priority Data

Dec. 13, 2013 (GB) .................................. 1322134.6

(51) Int. Cl.
*A61M 25/02* (2006.01)

(52) U.S. Cl.
CPC ....... *A61M 25/02* (2013.01); *A61M 2025/028* (2013.01); *A61M 2025/0213* (2013.01); (Continued)

(58) Field of Classification Search
CPC .......... A61M 25/02; A61M 2025/0206; A61M 2025/0213; A61M 2025/024;
(Continued)

(56) References Cited

U.S. PATENT DOCUMENTS

| | | |
|---|---|---|
| 5,720,713 A | 2/1998 | Hutchison |
| 5,916,199 A | 6/1999 | Miles |

(Continued)

FOREIGN PATENT DOCUMENTS

| | | |
|---|---|---|
| WO | 0168180 A1 | 9/2001 |
| WO | 2007024900 A2 | 3/2007 |

(Continued)

OTHER PUBLICATIONS

Great Britain Search Report from corresponding Great Britain Application No. GB1322134.6, dated Jul. 10, 2014.

(Continued)

*Primary Examiner* — Bhisma Mehta
*Assistant Examiner* — James D Ponton
(74) *Attorney, Agent, or Firm* — Workman Nydegger

(57) ABSTRACT

A medical device suitable for assisting in liquid proof shielding of a catheter application area on the body of a living creature is described. The device has a base element tightly placeable on a body area near the catheter application area, and a top element connectable with the base element. One of the base element or the top element is an element with a slit for holding a catheter tube or infusion line and the other element has a protrusion for closing the slit and for forming a feedthrough for the catheter when the elements are connected. A first portion for tightly fitting and a second portion for forming a liquid sealing element for the catheter is used.

15 Claims, 13 Drawing Sheets

(52) U.S. Cl.
CPC ............... *A61M 2025/0246* (2013.01); *A61M 2025/0253* (2013.01); *A61M 2025/0273* (2013.01)

(58) Field of Classification Search
CPC .. A61M 2025/0246; A61M 2025/0253; A61M 2025/026; A61M 2025/0266; A61M 2025/0273
See application file for complete search history.

(56) References Cited

U.S. PATENT DOCUMENTS

| | | | |
|---|---|---|---|
| 6,267,115 | B1 | 7/2001 | Marshel |
| 6,273,873 | B1* | 8/2001 | Fleischer ............... A61M 25/02 604/1 |
| 6,482,183 | B1 | 11/2002 | Pausch et al. |
| 2008/0167626 | A1 | 7/2008 | Beery et al. |
| 2011/0301541 | A1* | 12/2011 | White ................... A61M 25/02 604/164.04 |
| 2013/0018319 | A1* | 1/2013 | Abe ..................... A61M 25/02 604/174 |
| 2013/0150796 | A1* | 6/2013 | Souza ................... A61M 25/02 604/180 |
| 2014/0330247 | A1* | 11/2014 | Rosenberg ............. A61M 25/02 604/506 |
| 2015/0224285 | A1* | 8/2015 | Howell ................. A61M 25/02 604/180 |

FOREIGN PATENT DOCUMENTS

| | | |
|---|---|---|
| WO | 2010002393 A1 | 1/2010 |
| WO | 2013090903 A1 | 6/2013 |

OTHER PUBLICATIONS

International Search Report from corresponding PCT Application No. PCT/EP2014/077214, dated Mar. 17, 2015.

\* cited by examiner

SHOWER PATCH BARRIER DEVICES

FIELD OF THE INVENTION

The invention relates to the field of healthcare. More specifically it relates to a device for protecting an injury on the body of a living creature or a medical appliance applied to the body of a living creature, for example protecting against dirt and water.

BACKGROUND OF THE INVENTION

In healthcare, a catheter is used to provide an access to the human body for delivery of medicinal drugs, parenteral nutrition, blood or blood components or other liquids. The latter is typically used for patients that are ill or during the performance of surgical procedures. Depending on the type of liquid that needs to be delivered and sometimes also depending on the patient or his/her medical condition, different catheters and different methods of applying them can be selected.

A first type of catheter is the peripheral venous catheter. This catheter is inserted in a peripheral vein. A second type of catheter is a midline catheter. Such a catheter typically is between 8 and 25 cm long and is often placed in an upper arm vein. A third type of catheter is a central venous catheter which is placed into a large vein.

Still other types of catheters are peripherally inserted central catheters, tunnelled catheters, drainage catheters and port catheters. These catheters can be applied at several places on the human body, such as for example in the breast area of a patient.

A large number of patients needs to make use of catheters, such as for example central catheters, tunnelled catheters or port catheters, for a long period, e.g. weeks or months. It often is preferred to make use of a same catheter for a longer time period, as correctly positioning a catheter is time consuming and as replacing or re-introducing a catheter into the human body typically results in additional risks for infections and additional pain for the patient during installing.

A disadvantage of the use of a catheter is that it often limits the patient in actions they can take. For example, washing or taking a shower whilst a catheter or part thereof is applied to the human body may be difficult or impossible as it should under all circumstances be avoided that for example dirt, air or shower water enters the catheter. The latter may prevent proper operation of the catheter and, in some circumstances, could even lead to dangerous or life threatening situations.

In order to avoid such critical situations, often showering is prohibited for patients having a catheter applied. Adequate sealing of the catheter could prevent critical situations and could allow e.g. showering. Nevertheless, efficient and adequate sealing means are not widely spread yet. Often, non-suitable sealing means are applied such as for example non-suitable patches, parts of plastic bags, cling film, parts of plastic gloves, etc. These sealing means result in inaccurate sealing, are difficult to apply, cannot be applied according to standard handling, . . . . Overall, a lot of sealing means that are used in today's practice do not allow to operate according to good medical practice. Some specialised sealing means that have been brought on the market in the past years attempt to overcome these problems.

A first set of examples relates to a bag-type of device that can be placed over the bodily part where the catheter is applied. The exit side of the bag-type device typically is provided with a glue strip to glue the bag to the bodily part. In U.S. Pat. No. 5,720,713, the system is provided with a feedthrough for a catheter, the feedthrough being made in PU foam. Alternatives are also brought on the market whereby the sealing is provided by folds created by folding the bag.

In a second set of examples, a patch is used for covering a catheter for use during bathing. In the example described in US patent application US2008167626, a multi-layered patch is provided whereby in one of the layers a feedthrough for a catheter is provided, the water tightness being provided by the sticking parts of the patch. Often two sticking patches to be applied on top of each other are used, requiring a significant amount of glue and material. Furthermore, it may be difficult to prevent liquid from running along the catheter anyway to enter the shielded area via the catheter. In yet another example, an additional clip is provided for putting it on the catheter and for avoiding that liquid enters the shielded area via the catheter. The latter is for example described in U.S. Pat. No. 6,267,115.

Some sealing devices have the disadvantage that the catheter needs to be de-coupled before bathing or showering. This de-coupling is a disadvantage, since it should be done by the medical staff, resulting in more time consumption for the caregiver, and a lower autonomy of the patient. Moreover, the decoupling increases the risk of clogging of the catheter and infections.

There is still room for improvement for providing an appropriate sealing.

SUMMARY OF THE INVENTION

It is an object of the present invention to provide a medical device allowing safe shielding of an infusion line, a catheter or catheter exit site applied to a human body.

It is an advantage of embodiments according to the present invention that a secure and waterproof barrier for a catheter or catheter exit site is obtained.

It is an advantage of embodiments according to the present invention that a medical device is provided that can be easily used, e.g. that can be used by the patient during showering or washing, without the need for assistance by an additional person or medical staff or caregivers. It is an advantage of embodiments of the present invention that the medical device can be used during e.g. washing or showering, without a lot of additional preparation actions to be performed.

It is an advantage of embodiments according to the present invention that the increased flexibility for taking a shower or washing allows the patient to improve his or her personal hygiene and feeling of well-being.

It is an advantage of at least some embodiments of the present invention that the risk on infections, e.g. catheter-related infections such as bloodstream infections, can optionally be low or reduced.

It is an advantage of embodiments of the present invention that it can render the patient more self-supportive, resulting in less time-consuming actions for medical staff or caregivers, providing more free time for performing other actions.

The above objective is accomplished by a method and device according to the present invention.

The present invention relates to a medical device suitable for assisting in liquid proof shielding of a catheter application area on the body of a living creature, the device comprising a base element having a deformable first side such that the base element is tightly placeable on a body area near the catheter application area, and a second side opposite the first side, a top element having a deformable first side connectable with the second side of the base element, one of the base element or the top element being an element comprising a slit for holding a catheter tube or infusion line and the other element comprising a protrusion for closing the slit and for forming a feed through for the catheter when the elements are connected, wherein a first portion of the element forming the slit and the protrusion is made of a first material and shaped for tightly fitting the catheter when it is in position and wherein the element forming the slit and/or the protrusion comprises a second portion formed in a second material, the second material being more soft and deformable than the first material, the second portion being adjacent to the first portion and being arranged so as to form a further liquid sealing element for the catheter.

Whereas the medical device is suitable for liquid tight sealing of a catheter area, medical devices are not restricted to that application and, for example, more generally the fixation of a catheter, e.g. a drainage catheter, is also envisaged by embodiments of the present invention.

It is an advantage of embodiments of the present invention that the soft material, e.g. internal ridges, can result in a better fixation of drainage catheters that have a diameter that is slightly deviating from the size for which the medical device is intended. The soft material also provides a good liquid tightness for drainage catheters that have a diameter that is slightly deviating from the size for which the medical device is intended. Slightly deviating may mean between 0.9 mm larger and 0.9 mm smaller than the diameter of the drainage catheter for which the medical device is intended.

It is an advantage of embodiments according to the present invention that a liquid-tight sealing is provided for a catheter feed through, e.g. allowing to keeping the catheter installed during bathing or showering.

It is an advantage of embodiments according to the present invention that a hard portion is provided allowing to fixedly position the catheter and that a softer portion is provided providing an additional sealing element.

It is an advantage of embodiments of the present invention that at least part of the slit and protrusion are made of hard material. When placed on the body only the deformable parts of the base element and of the top element will deform and ensure a waterproof connection with the body. The hard parts of the slit and protrusion will not deform and will ensure a secure connection with the catheter. The first portion may tightly fit the catheter and may be specifically developed for operation with certain types and sizes of catheters.

The first portion of the element may be embedded in the second portion of the element.

It is an advantage of embodiments that the hard material is embedded in the soft material. This ensures that, although the soft material is deformed to make a good connection with the body, the hard material remains in close—waterproof—contact with the soft material. Such a structure can be realized by overmolding or by separately producing the hard and the soft material and then sealing the hard and the soft material.

The device furthermore may comprise a foil for covering the catheter application area, the foil comprising a catheter exit site placeable between the base element and the top element.

It is an advantage of embodiments according to the present invention that accurate sealing of the full catheter application area can be performed and that the catheter may be kept installed during showering or bathing.

The second portion made of the second material may be deformable around the catheter tube or infusion line.

One of the base element or the top element may comprise also a second protrusion, the first protrusion and the second protrusion being made of the first material and being removable connectable on the other element.

It is an advantage of embodiments of the current invention that the top element and the base element can be securely attached to each other while it is still possible to disconnect them by opening the removable connection mechanism, e.g. a click mechanism, a clip mechanism, etc. The removable connection allows to easily place as well as easily remove the device.

The top element may comprise a holding portion for holding the top element during manipulation.

It is an advantage of embodiments of the current invention that the holding portion, e.g. a fin, on the top element allows the user to firmly hold the top element when manipulating, e.g. placing or removing it.

The top element may comprise a first holding portion and a second holding portion for holding the top element and wherein the first holding portion and the second holding portion are configured for, when pushing the holding portions simultaneously with respect to each other, opening the removable connection.

It is an advantage of embodiments of the current invention that pushing on both fins allows to open the clicking mechanism which allows to easily remove the top element from the base element.

In another embodiment, the holding portion is a single holding portion, allowing the user to manipulate, e.g. hold, the upper side of the snap.

The device furthermore may comprise an adhesive material at one or more of the first side of the base element, the second side of the base element, the first side of the top element such that the adhesive material assists in providing a liquid proof sealing.

The presence of the double sided adhesion layers assists in a waterproof connection between the parts of the device and between the base structure and the body.

The adhesive material may be a double-sided adhesive layer.

The adhesive material may be at least located at a peripheral position of a foil for covering the catheter application area.

The device may comprise a closing element for closing the slit in absence of a catheter, the closing element being a full replacement piece having the same cross-section as the catheter or infusion line.

It is an advantage of embodiments of the present invention that the device can be closed even when no catheter tube or infusion line is passing through the device. The slit typically is selected in size to fit the infusion line that needs to pass.

The base element and the top element may be made of watertight materials.

The first portion may be configured with respect to the second portion such that, in a connected state of the first and second element with a catheter being positioned, if the first portion is holding the catheter, the second portion is pressed against the catheter for generating a further sealing effect.

The base element may comprise the slit and the top element may comprise the protrusion.

The second material may be ethylene propylene diene monomer rubber or a PVC material.

The foil may be transparent thus allowing visible inspection.

In some embodiments, the base element and the top element are adapted in shape so as to create, when the base element and the top element are snapped into each other, a smooth upper surface of the medical device.

The medical device may comprise a transparent foil for sticking over the catheter area and the smoothed upper surface.

The present invention also relates to the use of a medical device as described above for liquid proof shielding of a catheter application area on a body of a living creature.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
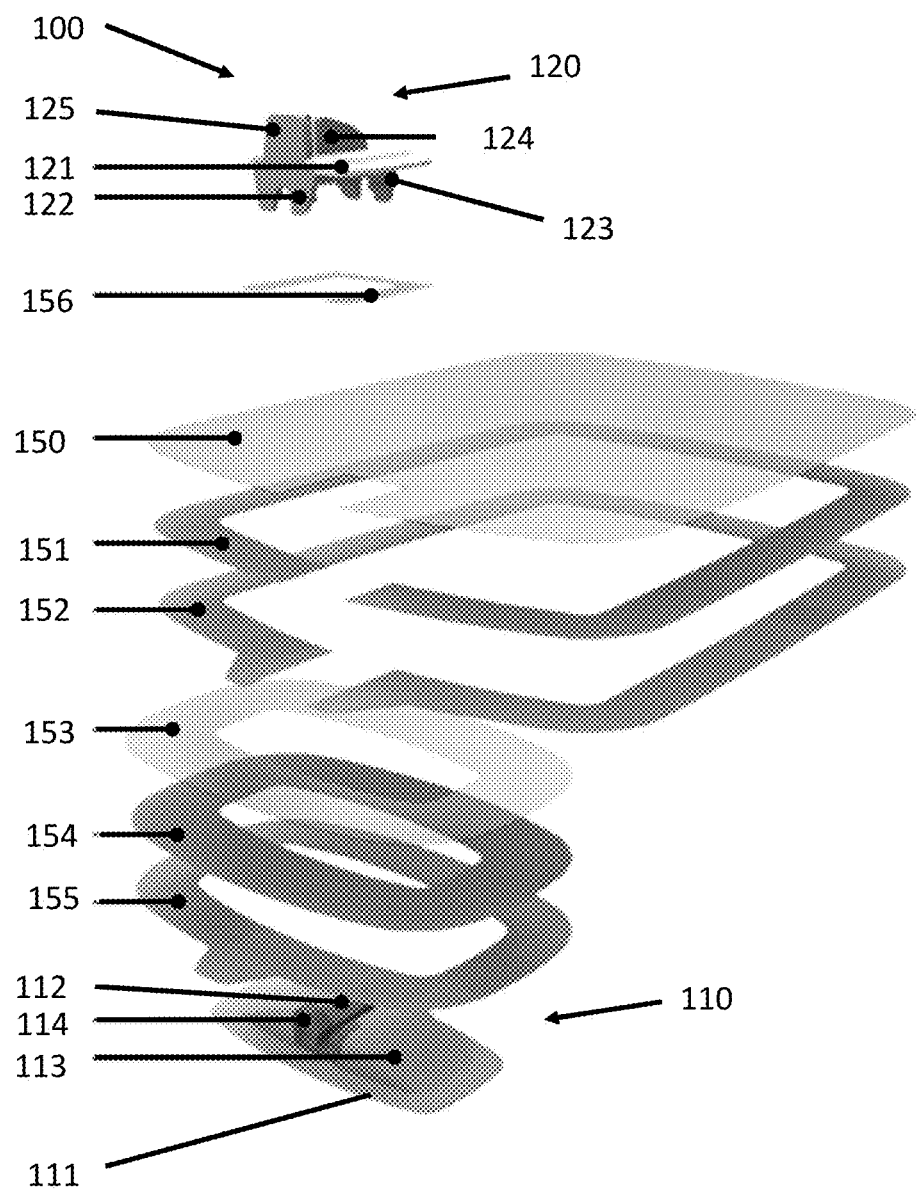
FIG. 1 provides a schematic 3D view of different components comprised in a medical device in accordance with embodiments of the present invention.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly, it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Where in embodiments of the present invention reference is made to "abase element", reference is made to the part of the device that is fixable (e.g. glued) to the patient's skin. It has a deformable first side such that a good waterproof joining between the skin and the base element is possible.

Where in embodiments of the present invention reference is made to "atop element", reference is made to the part of the device that is mountable on top of the base element.

In a first aspect the present invention relates to a medical device suitable for assisting in liquid proof shielding of a catheter application area on the body of a living creature. The medical device allows a living creature, e.g. a patient, to take a shower, wash or bath with a catheter installed, thus resulting in more patient comfort. In some embodiments, the medical device encompasses the sealing element providing a feedthrough for the catheter tube or infusion line alone, whereas in other embodiments, also the covering foil is part of the medical device. Although the medical device can advantageously be used for liquid proof shielding of a catheter application area, medical devices according to embodiments of the present invention are not restricted thereto and can also be applied e.g. merely for fixating a catheter, e.g. a drainage catheter. The medical device may in some embodiments be considered as a consumable for single use. According to embodiments of the present invention, the medical device comprises a base element having a deformable first side such that the base element is tightly placeable on a body area near the catheter application area, and a second side opposite the first side. The medical device also comprises a top element having a deformable first side connectable with the second side of the base element. In the medical device, one of the base element or the top element thereby is an element comprising a slit for holding a catheter tube or infusion line and the other element comprising a protrusion for closing the slit and for forming a feedthrough for the catheter when the elements are connected. The first portion of the element forming the slit and the protrusion is formed in a first material and shaped for tightly fitting the catheter when it is in position. The element forming the slit and/or the protrusion also comprises a second portion formed in a second material, the second material being more soft and deformable than the first material and the second portion being adjacent the first portion and being arranged so as to form a further liquid sealing element for the catheter. The second material may have a shoreness between 25 and 65 as measured with a durometer. The tensile modulus of the first material may be between 1000 and 2500 MPa.

In the particular embodiments and examples described below, the slit portion for receiving the catheter tube or infusion line is shown and described to be in the base element and the protrusion is in the top element. The person skilled in the art will realize that the present invention also encompasses devices where the slit is provided in the top element and the protrusion is in the base element. Nevertheless, in view of ease of application of the medical device, positioning of the catheter tube or infusion line in a slit in the base element seems preferred.

By way of illustration, embodiments of the present invention not being limited thereto, some exemplary embodiments will further be discussed, illustrating standard and optional features of embodiments of the present invention. Reference will be made to the different drawings.

FIG. 1 illustrates an exploded view of a medical device according to a first particular embodiment of the present invention. The medical device allows forming a secure and waterproof barrier for a catheter application area. The medical device is based on a foil 150 used for sealing a body area where a catheter is applied, as well as a component for sealing the feed through of a catheter tube or infusion line. The latter allows that the catheter can be kept in function during showering or bathing of a patient. The use of a specific component for sealing the feed through allows a proper sealing, as using only a sticking foil typically results in leaving a weak sealing at the point where the catheter tube or infusion line leaves the foil. Such weak sealing points are vulnerable for water, soap or dirt coming in as well as for loosening of the medical device at that position.

Figure 4:
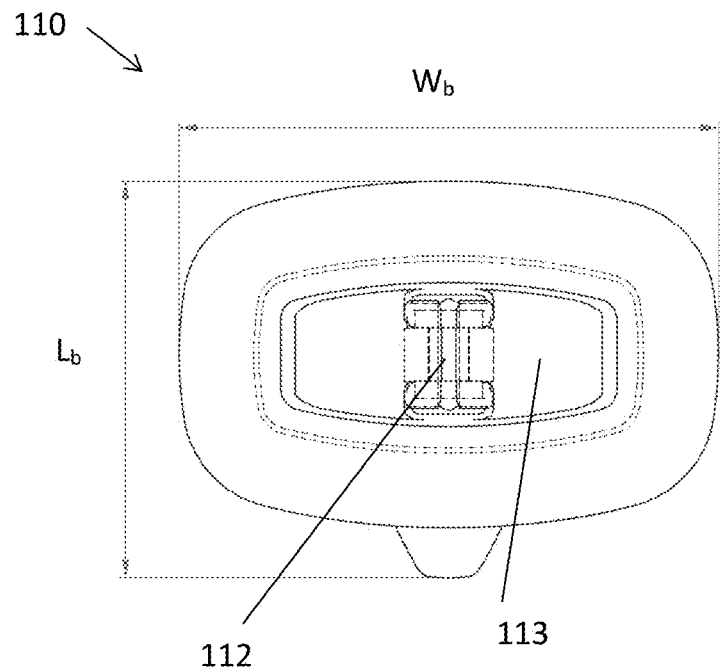
FIG. 4 provides a schematic top view of a base element in accordance with embodiments of the present invention.
Figure 5:
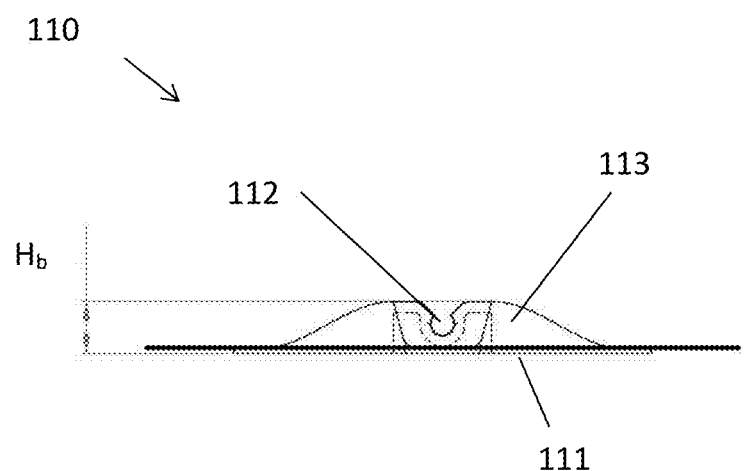
FIG. 5 provides a schematic front view of a base element in accordance with embodiments of the present invention.
Figure 6:
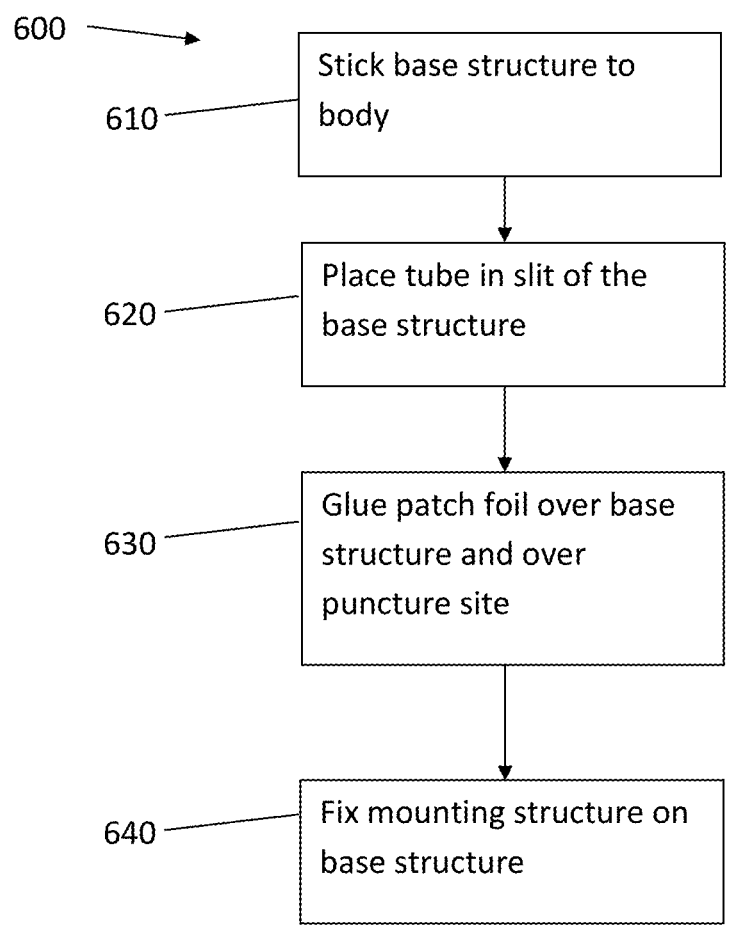
FIG. 6 provides method steps of an exemplary method for applying a device in accordance with embodiments of the present invention.
Figure 7:
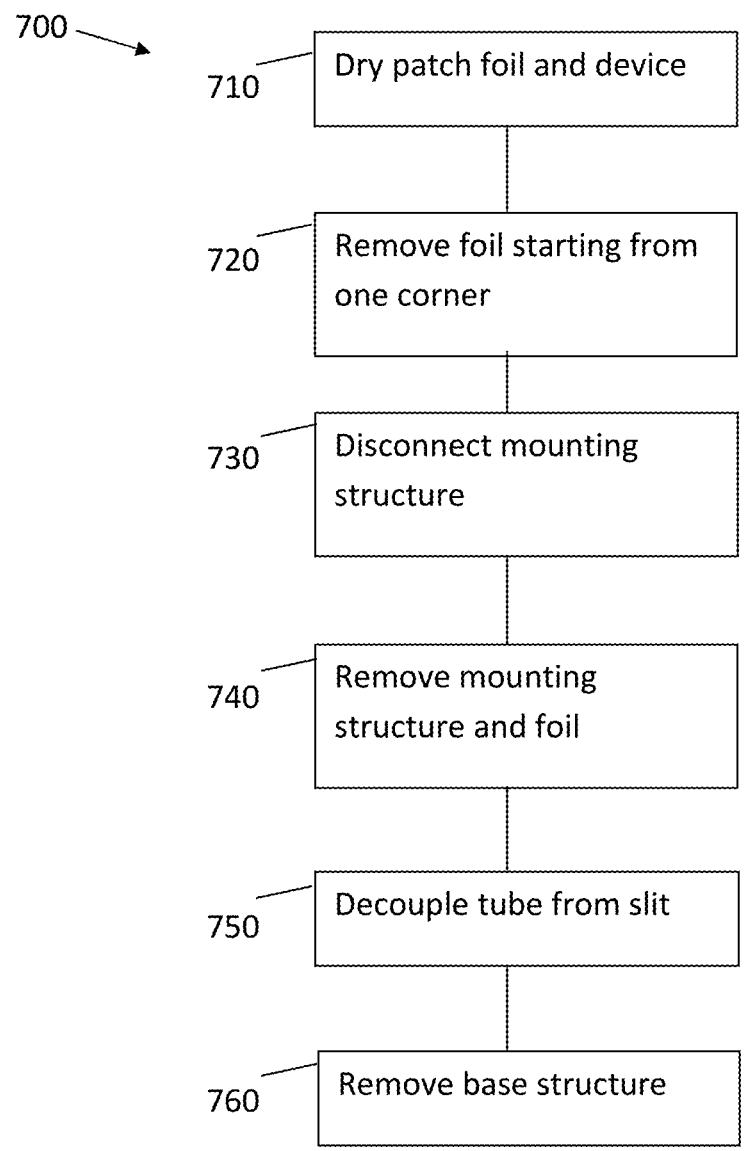
FIG. 7 provides method steps of an exemplary method for removing a device in accordance with embodiments of the present invention.

The device 100 according to the first embodiment comprises a base element 110 shown in FIG. 1, FIG. 4 and FIG. 5. The base element 110 has a deformable first side 111 such that the base element is tightly placeable on a body area near the catheter exit site of the foil. In the present embodiment the base element is glued to the body using a double sided adhesion layer, although embodiments are not limited thereto and another glue or other fixing material also may be applied. This adhesion layer can be at the bottom side of the base element, i.e. between the base element and the skin. The adhesion layer can also be around the base element covering the edge of the base element and the skin. An example of a fixation means whereby the edges of the base element are fixed to the skin by providing a tape 154 over the edge and the surrounding skin is illustrated in FIG. 1. The base element 110 has a slit 112 for holding a tube on a second side 113 opposite to the first side 111. The base element 110 is made of waterproof material. At least part of the base element 110 is made of a deformable material 111, 113. In embodiments of the present invention also the form may be selected for providing a good adaptability to the body underneath. The thickness ($H_m$) may for example be at his thickest near the slit 112 and gets thinner towards the edges, as illustrated in FIG. 5. This results in so-called deformable wings. These wings adjust more easily to the body shape than thicker portions. The exemplary embodiments in the figures show a wing shaped base element 110. Embodiments of the present invention are however not limited thereto. In one example, the soft material is ethylene propylene diene monomer rubber (EPDM rubber). One example of a shape and dimensions of the base element that may be used are indicated in FIG. 4 and FIG. 5. In embodiments of the present invention the length $L_b$ of the base element may for example be between 10 mm and 150 mm, for example between 50 mm and 100 mm, for example 74.4 mm. In embodiments of the present invention the width $W_b$ of the base element may for example be between 20 mm and 200 mm, for example between 80 mm and 120 mm, for example 101 mm. In embodiments of the present invention the maximum height $H_b$ of the base element may be between 4 mm and 20 mm, for example between 8 mm and 12 mm, for example 8.9 mm.

The medical device 100 also comprises a top element 120. The top element 120 typically may have a deformable first side 121. This deformable first side 121 can be deformed such that a waterproof sealing between the base element 110 and the top element 120 can be realized. In one example according to an embodiment of the present invention where the base element 110 is wing shaped, the deformable first side 121 of the top element 120 is deformable to provide a waterproof sealing with the wing shaped top element 110.

Figure 2:
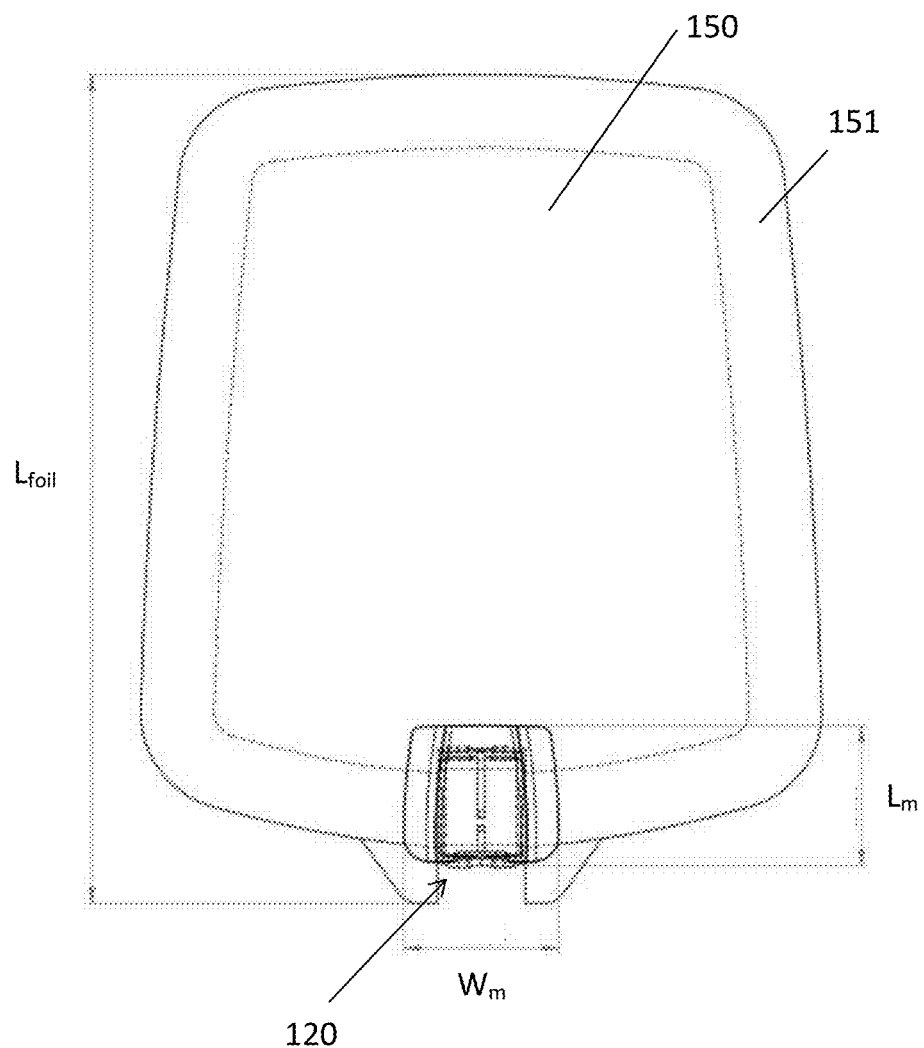
FIG. 2 provides a schematic top view of a foil and top element in accordance with embodiments of the present invention.
Figure 3:
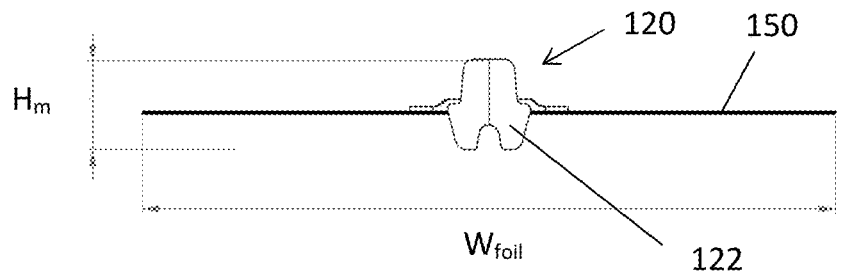
FIG. 3 provides a schematic front view of a foil and top element in accordance with embodiments of the present invention.

Moreover, the top element 120 has a protrusion 122 for closing the slit 112, e.g. when a catheter tube or infusion line is present therein, when the top element 120 is mounted on the base element 110. The top element 120 typically is made of waterproof material. The dimensions and shape of an exemplary top element are indicated in FIG. 2 and FIG. 3. In embodiments of the present invention the length $L_m$ of the top element may be between 15 mm and 50 mm, for example between 25 mm and 30 mm, for example be 28.6 mm. In embodiments of the present invention the width $W_m$ of the top element may for example be between 10 mm and 80 mm, for example between 25 mm and 35 mm, for example be 31.6 mm. In embodiments of the present invention the height $H_m$ of the top element, comprising the protrusion may for example be between 10 mm and 40 mm, for example between 15 mm and 20 mm, for example be 17.8 mm.

When mounted, the base element 110 is fixed against the body, the catheter exit site of the foil 150 is in between the base element 110 and the top element 120, and the catheter tube or infusion line is in the slit of the base element. The protrusion 122 pushes against the tube thereby realizing a first sealing preventing water to enter alongside the tube. The inside diameter of the slit 112 is adapted towards the outside diameter of the tube such that the tube fits tightly in the slit 112 preventing water to enter the sealed volume where the catheter is injected. In embodiments of the present invention at least a first portion of the element forming the slit 112 is made of hard material 114. The hard material is shaped such that the catheter tube or infusion line fits tightly with the slit. Also at least a first portion of the protrusion 122 is made of hard material fitting tightly with the opposite side of the tube when mounted. When deforming and gluing the top element 110 to the body only the deformable first side 111 will deform. The parts of the slit 112 made of hard material will not deform and therefore their shape will remain matching with the shape of the tube. This provides a first sealing element for avoiding liquid to enter the sealed volume between the slit 112 and the catheter tube or infusion line. The hard material enables a good fit between the tube and the slit 112 and guaranties that the shape does not change when deforming the base element 110. Instead of being adapted for a cylindrical tube the slit might be adapted for holding various shaped tubes. The hard material of the slit guarantees a constant pressure of the slit 112 on the tube. The fact that a first portion of the slit and protrusion is made in more hard material allows to accurately position and fix the catheter tube or infusion line.

A second portion of at least one of the base element and the top element is made of a soft deformable material. The soft deformable material provides an additional sealing for the catheter. Furthermore, it also guarantees a waterproof sealing between the body and the base element 110 and between the base element 110 and the top element 120. In some specific embodiments the part of the slit made of hard material 114 is embedded in the soft deformable material. This can be realized by overmolding. By embedding the hard material in the soft material the waterproof connection between the hard material and the soft material is ensured. For realizing the top element 120 overmolding is also a possibility as process for realizing a combined hard/soft structure.

Sealing may be provided via sealing rings in the slit and/or at the protrusion. Such rings may be appropriate in width and thickness for providing additional sealing. In some embodiments, one or more sealing rings may be present in both the base element, e.g. in the slit, and in the top element, e.g. at the protrusion so that additional sealing is created at all sides of the tube.

The foil 150 for sealing the catheter application area also may be considered part of the medical device, although embodiments are not limited thereto and may only relate to the sealing component providing a catheter feed through.

The foil 150 may have a high moisture vapor transmission rate such that vapor can leave the sealed volume. The latter prevents that the sealed volume gets humid because of sweating. In one example, the foil 150 is a polyurethane foil with a thickness of about 40 μm. The thickness of the foil may be selected so that the foil is sufficiently strong for avoiding tearing when the different components are handled. The area of the foil should be sufficient to cover the injection area, including the dressings already applied on the exit site. It thereby is an advantage that dressings already applied can be kept dry and therefore need not to be replaced after washing, bathing or showering. This saves time and materials. In one example the foil 150 is a Smith and Nephew EU40. This foil has a thickness of 36 μm, a weight of 38 g/m², a moisture vapor transmission rate of 1000 g/cm² per 24 hours at a temperature of 37° C. The width of the EU40 foil ($W_{foil}$ in FIG. 3) is between 50 mm and 1300 mm. The nominal length at maximum width ($L_{foil}$ in FIG. 2) is 1000 mm. In some embodiments of the present invention a double sided tape 151 is provided to glue the edge of the foil 150 on the skin. In embodiments of the present invention the width of the double sided tape may for example be between 40 mm and 10 mm preferably between 20 mm and 13 mm, more preferably equal to 15 mm. The tape could for example be a double coated tape 1577 from 3M. Any other foils or tapes used for wound care are also applicable in embodiments of the present invention.

The mounted device 100 as for example shown in FIG. 1 is in the present example a plastic device which allows to realize a waterproof connection with a foil 150 and which allows to realize a waterproof exit for a catheter tube or infusion line. The foil 150 fits between the base element 110 and the mounting device 120 such that the volume under the foil 150 is sealed from external water entering into the sealed volume.

In the particular example shown, embodiments not being limited thereto, the top element 120 comprises a first protrusion 122 and a second protrusion 123. The first protrusion 122 and the second protrusion 123 are made of hard material and are removable connectable on the base element 110, e.g. clippable, clickable, . . . . The parts of the base element 110 on which the first protrusion 122 and second protrusion 123 are connected are also made of hard material. The first protrusion 122 and the second protrusion 123 are illustrated in FIG. 1. Both protrusions 122, 123 comprise a thickening that fits in a narrowing of the base element 110. When mounted, the base element 110 and the top element 120 are pressed against each other using the clicking mechanism which is made of hard material. Since the parts of the base element 110 and top element 120 which are pressed against each other are soft deformable materials a good waterproof contact is ensured between both.

In embodiments of the present invention a holding portion 124, e.g. a fin, is present on top of the top element 120. This holding portion 124 can be used to hold the top element 120 when positioning the top element 120 on top of the base element 110 or when removing the top element 120 from the base element 110.

The holding portion may comprise a single holding portion, as described above, but alternatively also may comprise a plurality of holding portions. In embodiments of the present invention a first holding portion 124, e.g. fin 124, and a second holding portion 125, e.g. fin 125, are present on top of the top element 120. Pushing on both holding portions causes them to move with regard to each other. Thereby the thickened parts of the first and second protrusions 122, 123 are separated. Thereby the clicking mechanism is released. This allows to easily remove the top element 120 from the base element 110. An exemplary embodiment of a two-fin top element is illustrated in FIG. 1.

In some particular embodiments of the present invention an adhesive layer, e.g. a double sided adhesion layer or layer of adhesive, may be used between the first side 111 of the base element 110 and the body. This allows to firmly position the base element 110 on the patient's body and it ensures a waterproof connection between the skin and the base element. In embodiments of the present invention the adhesive layer for fixing the base element 110 is above the base element covering the edge of the base element and the and the body. This is illustrated in FIG. 1 where a double sided adhesion layer 154 is shown. It can be glued on the base element and the body after removal of the release paper 155. In the exemplary embodiment of FIG. 1 a patch foil 153 covers the other side of the adhesive layer 154.

In some particular embodiments of the present invention a double sided adhesion layer 151 is applicable between the base element 110 and the foil 150. The part of the foil where the catheter tube or infusion line exits the foil is glued using a double sided adhesion layer on the base element. The tube itself can be pushed in the slit 112 of the base element 110. The adhesion layer 151 between the foil 150 and the base element 110 ensures a waterproof connection between both. The double sided adhesion layer 151 covers the edges of the foil 150 over the circumference of the foil 150 which allow to glue the foil surrounding the injection area and thereby creating a sealed volume around the injection area. The double sided adhesion layer 151 is protected with a release paper 152. After removing the release paper, the base element can be glued to the body. Alternatively, a layer of adhesive may be used.

In some particular embodiments of the present invention a double sided adhesion layer 156 is present between the foil 150 or part thereof and the top element 120. This double sided adhesion layer 156 may assist in obtaining a waterproof connection between the top element 120 and the foil 110. An exemplary combination of foils and double sided adhesion layers is illustrated in FIG. 1. Alternatively, a layer of adhesive may be used.

In some particular embodiments of the present invention, parts that can be interconnected upfront may be connected via adhesive, but alternative techniques also may be used such as welding, laser welding, hot melting, etc.

Components of embodiments of the present invention, such as for example the base element and the top element, may be made using any suitable technology such as for example by overmoulding, by polyjet technology, by injection moulding, etc.

In the exemplary embodiments shown in the figures only one slit 112 is shown. However, the present invention is not limited thereto. Embodiments of the present invention may also comprise multiple slits thereby providing a waterproof exit for multiple tubes or catheters with more than 1 lumen.

Embodiments of the present invention can also be applied if no tube is present. Therefore, in some embodiments, the medical device also comprises a closing element 116, such as a piece having the same cross-section as the original tube, which can be placed in the slit instead of the catheter tube or infusion line. Thereby this piece seals the slit closing the feedthrough.

Figure 10:
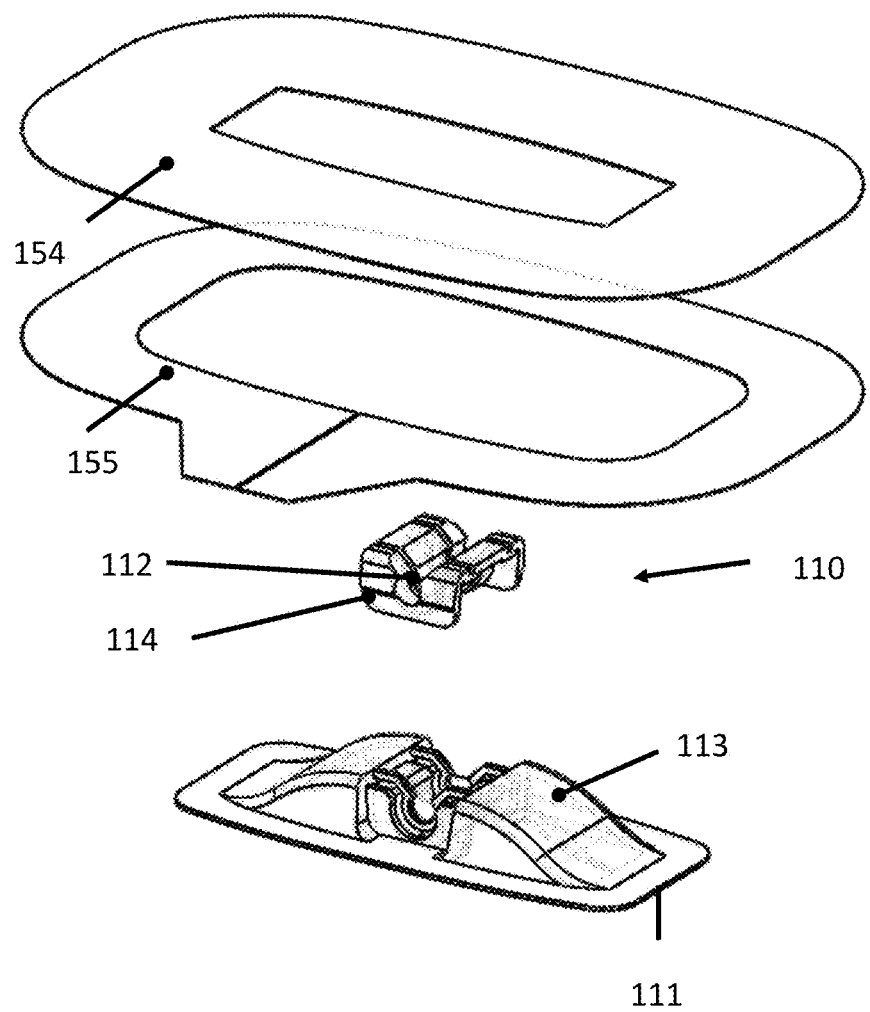
FIG. 10 provides a 3D line drawing of a base element in accordance with embodiments of the present invention.

A further exemplary embodiment is shown in FIG. 10. It shows a base element with a slit part 114 made of hard material. The slit part 114 comprises a slit 112 for holding a tube. The slit part made of hard material 114 can be mounted onto the soft part of the base element 110. The soft part comprising a deformable first side 111 and a second side on the opposite of the deformable first side. FIG. 10 also shows the double sided adhesion layer 154 and the release paper 155. In embodiments of the present invention the slit part made of hard material 114 is embedded in the soft part through overmolding. In the exemplary embodiment of FIG. 10 this is not the case. Here the soft part and the hard part are two pieces which can be mounted together.

Figure 11:
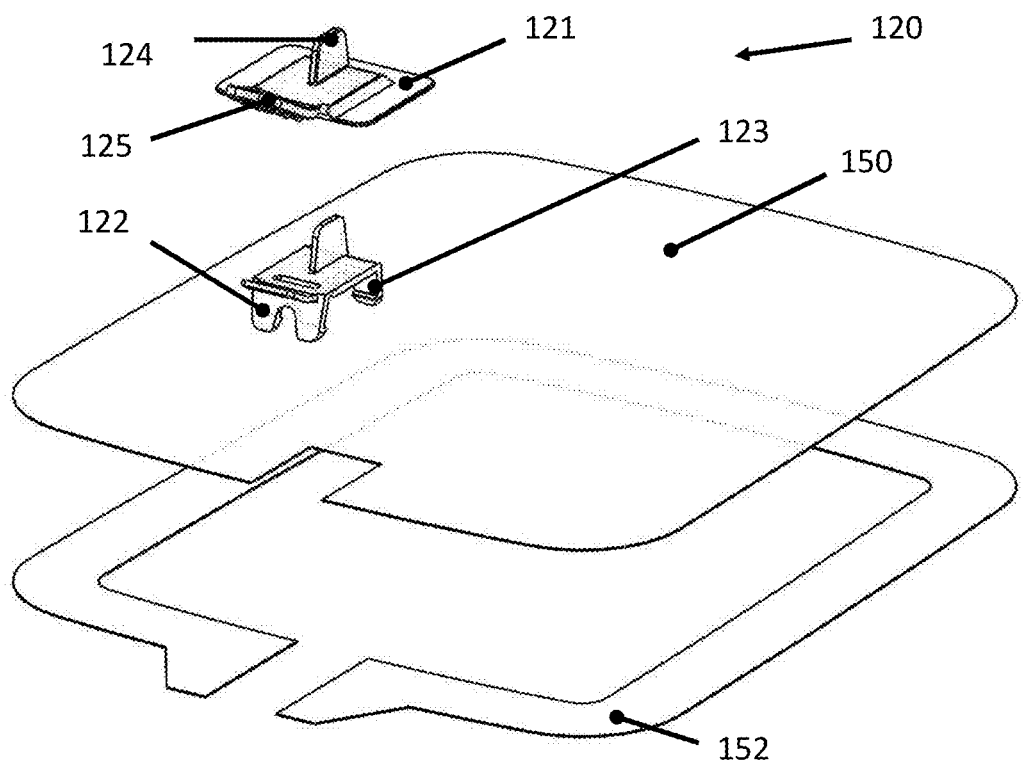
FIG. 11 provides a 3D line drawing of a top element in accordance with embodiments of the present invention.
Figure 12:
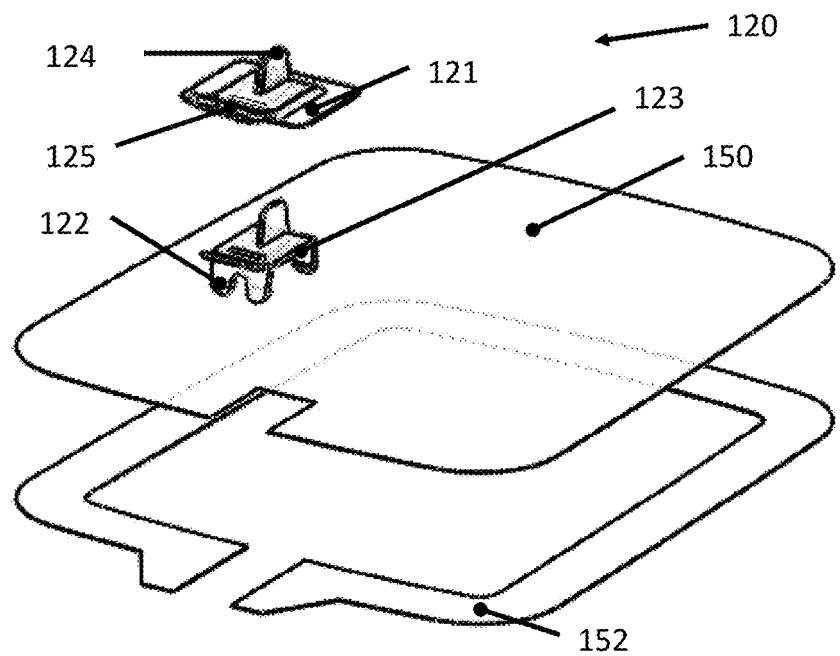
FIG. 12 provides a 3D line drawing of a base element and of a top element in accordance with embodiments of the present invention.
Figure 12:
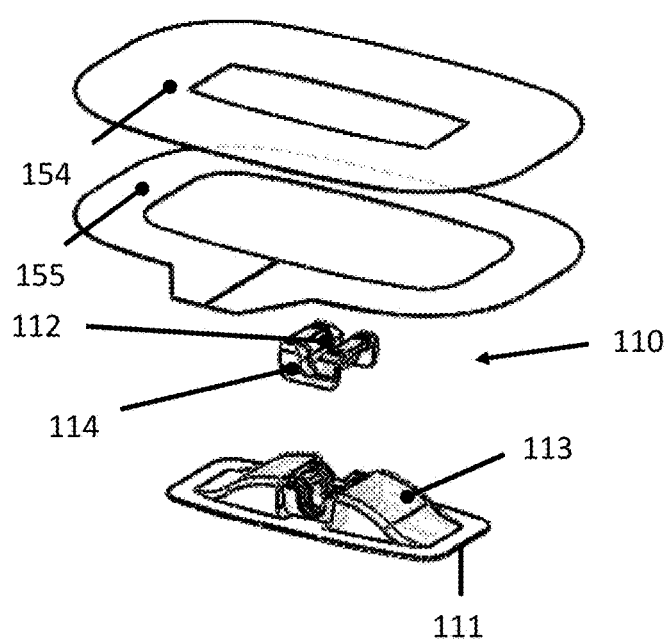
Figure 13:
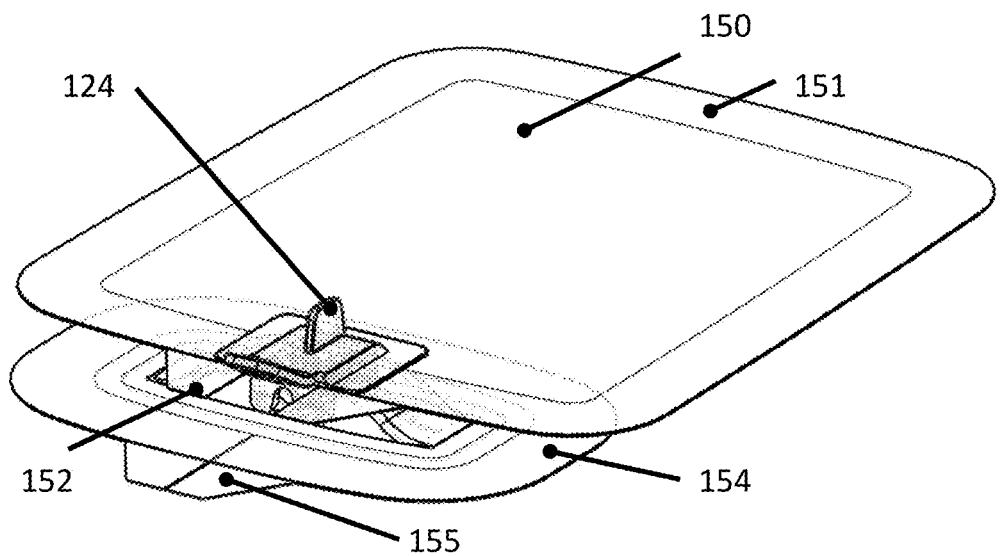
FIG. 13 provides a 3D line drawing of a base element and of a top element in accordance with embodiments of the present invention.
Figure 14:
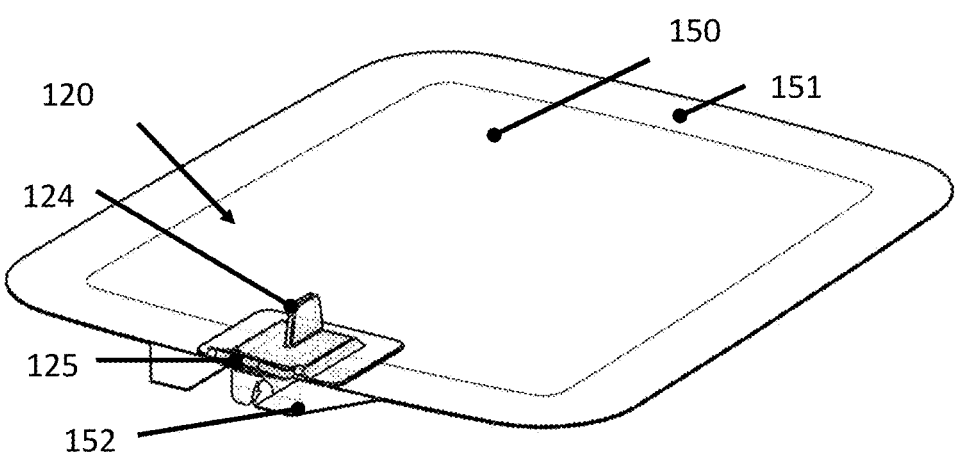
FIG. 14 provides a 3D line drawing of a base element and of a top element in accordance with embodiments of the present invention.
Figure 14:
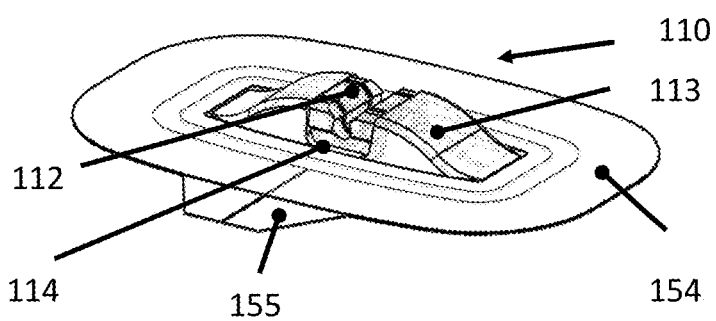
Figure 15:
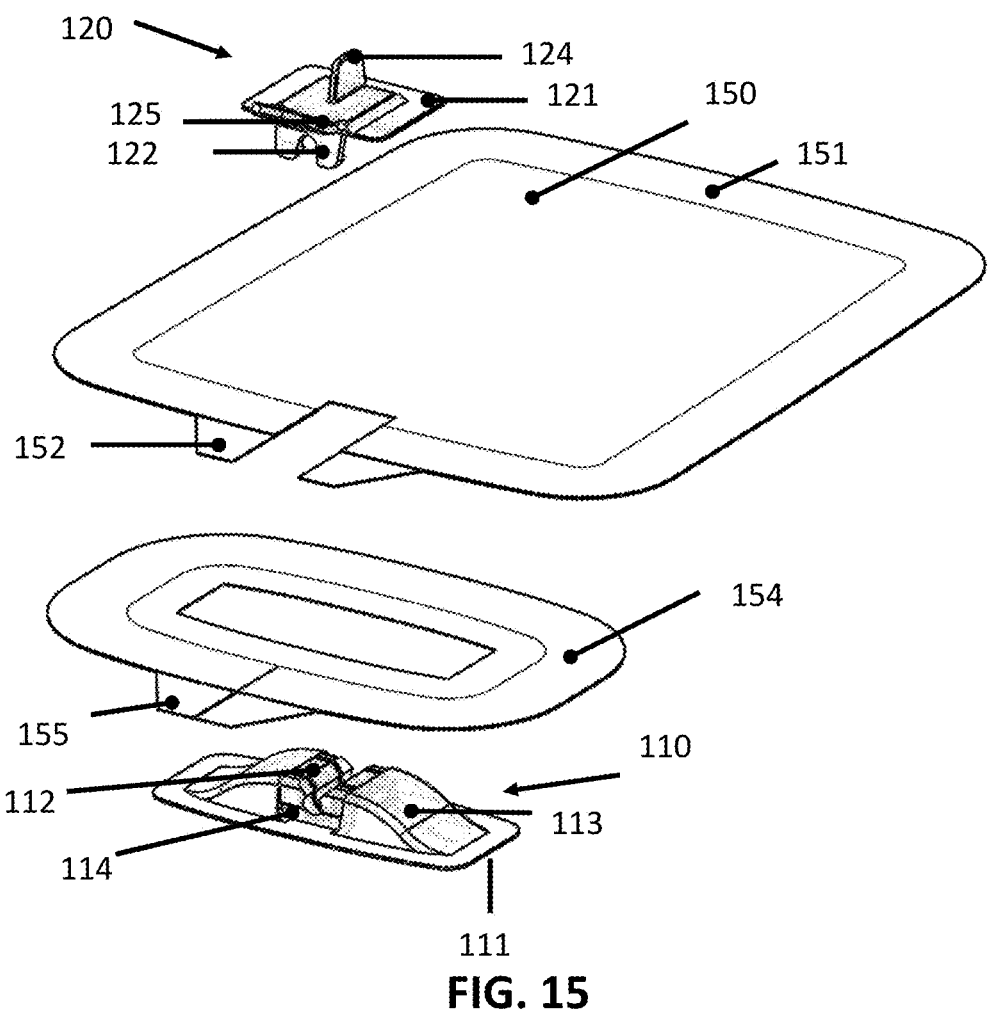
FIG. 15 provides a 3D line drawing of a base element and of a top element in accordance with embodiments of the present invention.

FIG. 11 shows a top element 120 in accordance with an exemplary embodiment of the present invention. The top element of the exemplary embodiment comprises two pieces: one hard piece and one soft piece. The hard piece comprises a first protrusion 122 and a second protrusion 123. The soft piece comprises a deformable first side 121, a first fin 124 and a second fin 125. A foil 150 can be attached to the skin using a double sided adhesion layer 151 (not visible in this figure). The adhesion layer is protected using a release paper 152.

FIG. 12, FIG. 13, FIG. 14 and FIG. 15 illustrate how the base element 110 of FIG. 10 and the top element 120 of FIG. 11 are to be mounted together. The double sided adhesion layer 151 is indicated on the foil 150 using dotted lines.

It is to be noticed that the thickness and/or the width of the components of the base element and/or top element can be selected such that they are robust with respect to handling.

Figure 16:
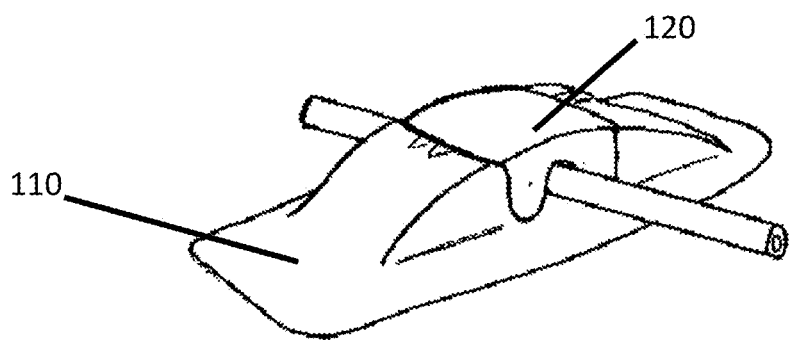
FIG. 16 provides a schematic view of a base element and top element according to an embodiment of the present invention, the base element and the top element being in snapped configuration.
Figure 17:
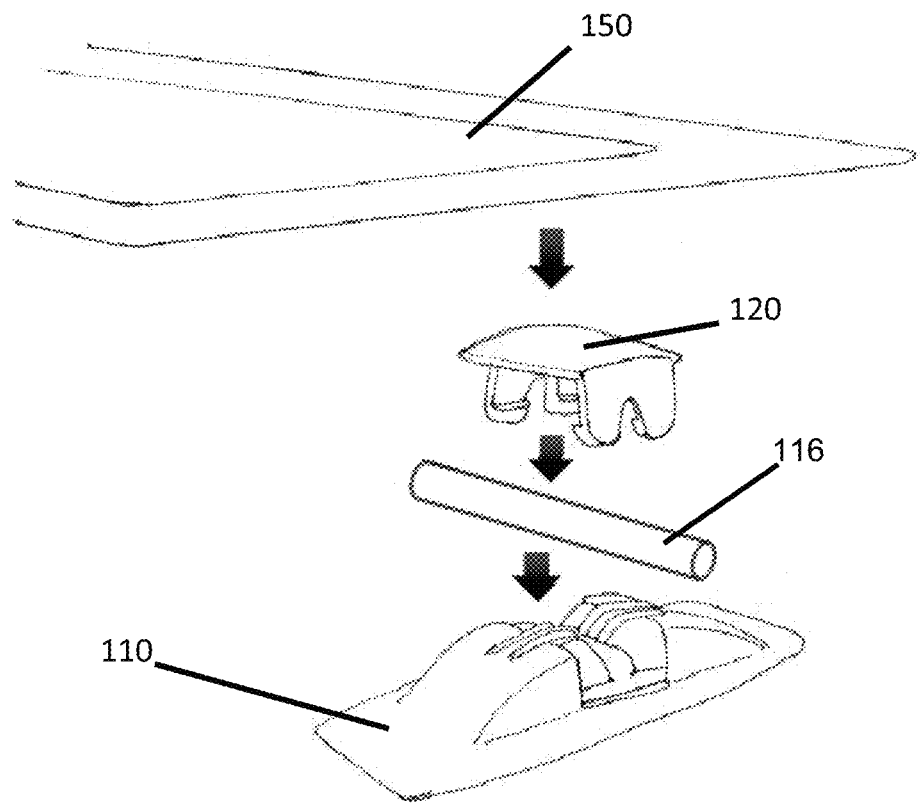
FIG. 17 provides an exploded view of a foil, base element, top element and closing element, according to an embodiment of the present invention.

In an alternative embodiment, a medical device according to an embodiment as described above is provided, whereby the upper surface of the top element does not comprise a holding portion or other extending portion, but whereby the upper surface of the top element, as well as the base element is shaped such that, when snapped into each other, the upper surface of the medical device, i.e. the surface not facing the skin of the patient, is a smooth surface. According to the present embodiment, the transparent foil for covering the catheter area is not pre-fixed to the top element or base element, but is initially separated from these components. For use, the transparent foil for covering the catheter area may be provided over the top element and the base element, whereby it is advantageous that the upper surface of the medical device is smooth. In contrast to, for example FIG. 14, no opening is required in the transparent foil for allowing portions of the top element to pass. The transparent foil thus may have a conventional shape, e.g. convex shape such as a rectangular shape, a rectangular shape with rounded corners, a circular shape, . . . . It is an advantage of a medical device according to the present embodiment that it can be easily manufactured with a limited cost. It is an advantage of a medical device according to the present embodiment that the base element and the top element (the snap) can be used longer on the body, i.e. that these can remain longer at the skin without failure. The transparent foil can be replaced when required, even without removing the base element and the top element. Where applicable the top element and the base element can further have features and advantages of embodiments described above. In FIG. 16 the top element and base element are shown in snapped position. FIG. 16 also illustrates the smooth surface. In FIG. 17, the medical device is illustrated in exploded view, whereby both components of the medical device are shown together with a portion of a catheter that needs to be fixed.

In one aspect, embodiments of the present invention also relate to the use of a medical device according to the first aspect for shielding a catheter application area. The use of such a medical device is, by way of illustration, embodiments of the present invention not being limited thereto, illustrated by exemplary method 600 for applying the medical device 100 and exemplary method 700 for removing the same device 100.

In the exemplary method the device 100 is prepacked in a single pouch. The pouch comprises the base element 110, the top element 120 and the foil 150. After opening the pouch and taking out the different components the first step for applying the device 100 is to stick 610 the base element 110 to a part of the body below the tube. In embodiments of the present invention this may be a catheter tube or infusion line, however any type of tube/wire is possible. In embodiments of the present invention the base element 110 has a double sided adhesive tape on the deformable first side 111. In embodiments of the present invention this tape is used to stick 610 the base element 110 to the skin after removal of the release paper. The base element is positioned below the tube not too far from the injection place.

In a second step 620 the tube is placed in the slit 112 of the base element 110. The slit 112 in the base element 110 allows to click the tube into the slit 112.

In a third step 630 the foil 150 is glued 630 over the base element 610 and over the puncture site. In embodiments of the present invention a double sided adhesion layer 151 serves as gluing means.

Figure 8:
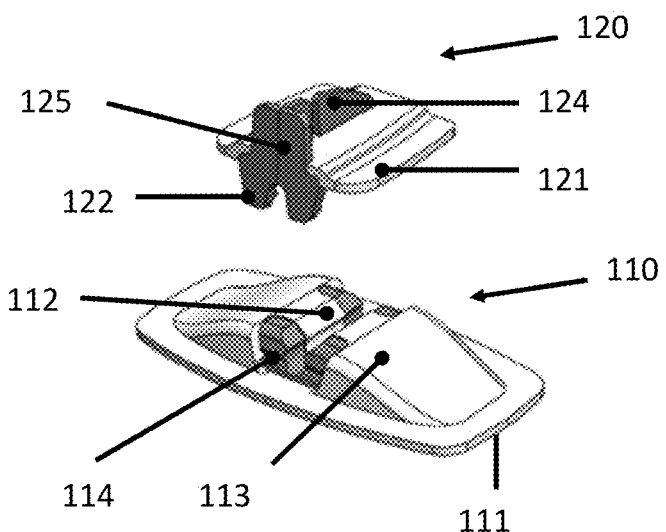
FIG. 8 provides a 3D schematic view of a mounting and base element in accordance with embodiments of the present invention.
Figure 9:
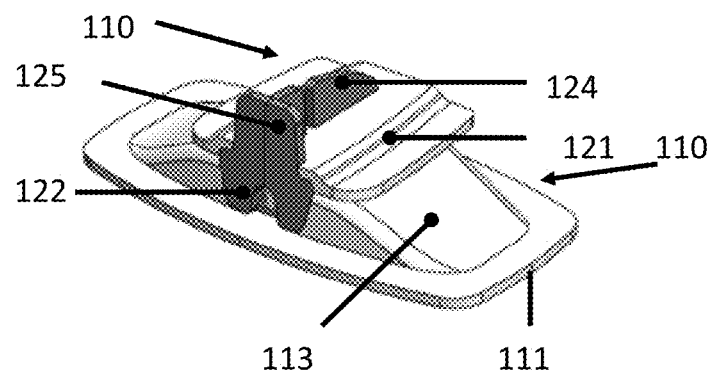
FIG. 9 provides a 3D schematic view of atop element mounted on a base element in accordance with embodiments of the present invention.

In a fourth step 640 the top element 120 is fixed over the base element 110 such that the top element 120 together with the base element 110 and the sealing 150 form a waterproof volume over the puncture site. This fixing might be done through a clicking mechanism provided by a first protrusion 122 and a second protrusion 123. The clicking mechanism thereby insures a waterproof sealing between the base element 110, the top element 120 and the tube. FIG. 8 shows the base element 110 and top element 120 before they are mounted. FIG. 9 shows a mounted setup. In embodiments of the present invention the foil 150 is glued to the skin only after clicking the top element 120 to the base element 110. Therefore, the release paper 152 is removed and the foil 150 is glued to the skin surrounding the catheter application area. To prevent folds in the foil 150, the foil is glued by moving the hand outwards over the foil 150.

The catheter application area is now sealed allowing the patient to wash himself or to take a shower.

An exemplary method 700 for removing the device 100 which is forming a shielding of a catheter application area may be as follows. The method comprises a first step 710 wherein the device 100 and the foil 150 are dried using a towel.

In a next step 720 the foil 150 can be detached starting from one corner of the foil 150 and by pulling the foil 150. Preferably the foil is pulled in a corner of 180°.

Next, in step 730, the top element 120 is disconnected from the base element 110. In embodiments of the present invention a fin 124 is present on the top element 120. This allows the user to have a good grip on the top element for removing it. In embodiments of the present invention a first fin 124 and a second fin 125 are present on top of the top element 120. By moving the first and second fin relative to each other (for example by pushing them towards each other) the clicking mechanism is released enabling the user to remove the top element 120 from the base element 110.

Once decoupled, both the top element and the foil 150 can be removed (step 740).

In a next step 750 the tube is decoupled from the slit 112 of the base element 110. This is done by lifting the tube out of the slit 112.

In a last step 760 the base element is removed from the skin by taking it on one corner and by lifting that corner. After this step the complete shower sealing is removed.

As indicated above, the medical device may be suitable for fixation of a catheter, e.g. a drainage catheter such as for example a transcutaneous drainage catheter. A percutaneous drainage catheter is a drainage catheter that exits the body through the skin. It is known that such drainage catheters need to be fixated in order for them not to shift or move. The transcutaneous drainage catheter has a similar sealing system as the shower patch described above, whereby the drainage catheter is fixed in an opening and a liquid tight sealing is provided. Typically, the medical device for fixation of the drainage catheter is positioned close to the exit-site of the catheter at the skin.

Figure 18:
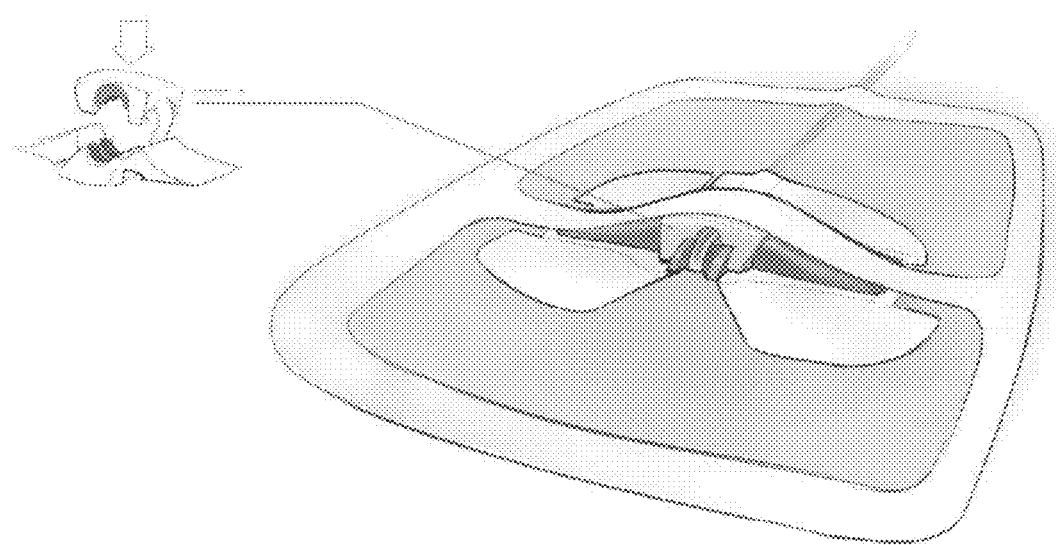
FIG. 18 illustrates a medical device for fixating a drainage catheter according to an embodiment of the present invention.

An exemplary embodiment of a medical device for providing fixation of a drainage catheter is shown in FIG. 18. The medical device comprises the same features as described in previously described embodiments, but the upper side of the patch or top element has a smooth surface (no holding portion is provided), so that an adhesive bandage can be provided in a liquid tight manner and such that a patient can lie on the medical device without it being uncomfortable. FIG. 18 illustrates the patch comprising a base element, a top element that can be connected to the base element. As in the other embodiments, either the base or the top element could comprise a slit for holding the drain catheter and the other comprises a protrusion for closing the slit and for forming a feedthrough for the catheter when the elements are connected. Furthermore, a first portion of the element forming the slit and the protrusion is made of a first material and shaped for tightly fitting the catheter when it is in position and wherein the element forming the slit and/or the protrusion comprises a second portion formed in a second material, the second material being more soft and deformable than the first material, the second portion being adjacent the first portion and being arranged so as to form a further liquid sealing element for the catheter. It is to be noticed that, as described above, the fixation of the catheter, in this case the drainage catheter, is obtained by inducing a mechanical tension from the top element, whereby a soft and a hard material is combined. The latter assist in a good fixation, which is at the same time liquid tight.

The medical devices may be produced for a drainage catheter having a specific diameter. Nevertheless, by using a soft material, a good fixation and liquid tightness of drainage catheters that have a diameter that is slightly deviating from the size for which the medical device is intended can also be obtained. Slightly deviating may mean between 0.9 mm larger and 0.9 mm smaller than the diameter of the drainage catheter for which the medical device is intended.

As indicated, the top element advantageously comprises a smooth upper surface such that an additional adhesive bandage (patch) can be positioned on top of the fixation elements and the fixation element as well as the entry site of the catheter can be sealed off from water, during e.g. washing or showering. An adhesive transparent bandage can be positioned over the top element and the drain-patch, so contact with water, e.g. for washing, does not need to be avoided. In one example, such a transparent adhesive bandage may be made of polyurethane, whereas the adhesive layer may be an acryl-based glue. Other materials nevertheless also can be used. It is an advantage that no water can come into contact with the position where the catheter is entering the skin. If the top element is rounded in design, the liquid tight positioning of a transparent adhesive bandage can even be performed more easy. The transparent adhesive bandage can be replaced after washing/showering.

In some embodiments of the shower patch for catheters in general or drainage catheters, the fixation of the catheter may be such that by fixating the catheter the catheter does not make a sharp curvature. The medical device therefore may comprise a guiding means, provided as part of the base element, the top element or as separate portion and allowing to guide the catheter to make a smooth curvature. The guiding means may provide a smooth curving surface against which the catheter can be positioned, e.g. a portion of the catheter between the entry site on the skin and the position where the catheter is fixated between the top and the base element can be positioned against this smooth curving surface of the guiding element.

In this way the guiding means is a means for anti-kinking of the catheter, thus avoiding unwanted twists or bends in the catheter.

As indicated above, it is an advantage of at least some embodiments of the present invention that the top element, also referred to as snap, can have a smooth design, e.g. a rounded design. It may comprise soft material. This allows that a user can lay on the patch, without this being uncomfortable. The latter may for example especially relevant if a nephrostomy drain is considered, since such a drain typically enters the body at the back of the patient, whereby when using conventional fixation, the patient cannot lay on the back. The fact that also soft material is used, results in that a cushioning effect occurs.

Figure 19:
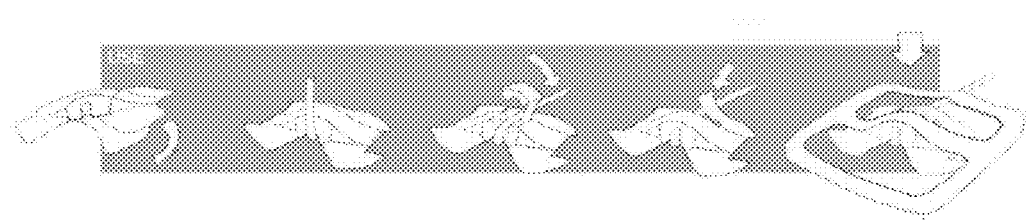
FIG. 19 illustrates different states of a medical device as described in FIG. 18, as obtained during application of the medical device to a drainage catheter in a patient's body.

By way of illustration, embodiments of the present invention not being limited thereto, an example of how to apply the catheter fixating medical device is shown in FIG. 19. FIG. 19 illustrates from left to right the different states of the catheter fixating medical device during the different steps of applying the medical device. In a first step, the release liner is removed to expose the adhesive to be able to stick the base element (optionally with the top element being connected to it) to the body. Once the release liner is removed, the base element (optionally with the top element being connected to it) is positioned close or as close as possible to the exit site. In a further step, if the top element is positioned on the base element, the top element or cap is removed from the medical device and the drain is positioned in the gap of the base element. The drain is then secured or fixated by connecting the top element (also referred to as cap) on the base element. The drain is then further tucked under the patch. Finally, a protective patch (also referred to as protective adhesive bandage) is positioned over the drain patch for allowing washing or showering.

In another aspect, the present invention also relates to the use of a medical device as described in the first aspect for fixating a catheter on a body of a living creature. In other words, the application of the medical device is not restricted to liquid tight shielding applications, although the medical device is especially suitable for it, but also extends to more generally fixating a catheter to the body of a living creature. Such a catheter may be any type of catheters, such as for example an intravenous catheter or a drainage catheter. For the use, a method can for example be applied as described in the second aspect, although embodiments are not limited thereto.

The invention claimed is:

1. A medical device suitable for assisting in liquid proof shielding of a catheter application area on the body of a living creature, the device comprising:
   a base element having a deformable first side such that the base element is tightly placeable on a body area near the catheter application area, and a second side opposite the first side;
   a top element having a deformable first side connectable with the second side of the base element, one of the base element or the top element being an element comprising a slit for holding a catheter tube or infusion line and the other of the base element or the top element comprising a protrusion for closing the slit and for forming a feedthrough for the catheter tube or infusion line when the base element and top element are connected;
   a foil for covering the catheter application area, the foil comprising a catheter exit site placeable between the base element and the top element;
   an adhesive material at one or more of the first side of the base element, the second side of the base element, and the first side of the top element such that the adhesive material assists in providing a liquid proof sealing;
   wherein the top element and the base element each comprise a first portion made of a first material and shaped for tightly fitting the catheter tube or infusion line when the catheter tube or infusion line is positioned in the slit;
   wherein the top element and/or the base element comprise(s) a second portion made of a second material, the second material being more soft and deformable than the first material; the first portion of the top element and/or the first portion of the base element being embedded in the second portion of that element; the second portion of that element being adjacent the first portion of that element and being arranged so that, if the first portion of that element is holding the catheter tube or infusion line, the second portion of that element is pressed against the catheter tube or infusion line for generating a liquid sealing element for the catheter tube or infusion line;

wherein the base element and the top element are adapted in shape so as to create, when the base element and the top element are snapped into each other, a smooth upper surface of the medical device.

2. A medical device according to claim 1, wherein the second portion of the top element and/or the second portion of the base element is deformable around the catheter tube or infusion line.

3. A medical device according to claim 1, wherein the protrusion is a first protrusion, wherein one of the base element or the top element comprises a second protrusion, the first protrusion and the second protrusion being made of the first material and being removably connectable on the element not comprising the second protrusion.

4. A medical device according to claim 1, wherein the top element comprises at least one holding portion for holding the top element during manipulation.

5. A medical device according to claim 4, wherein the at least one holding portion comprises a first holding portion and a second holding portion for holding the top element and wherein the first holding portion and the second holding portion are configured for, when pushing the holding portions simultaneously with respect to each other, opening a removable connection between the top element and the base element.

6. A medical device according to claim 1, wherein the adhesive material is a double-sided adhesive layer or wherein the adhesive material is at least located at a peripheral position of the foil.

7. A medical device according to claim 1, the medical device being configured for fixating a drainage catheter.

8. A medical device according to claim 1, the device comprising a closing element for closing the slit in absence of the catheter tube or infusion line, the closing element being a full replacement piece having a cross-section that is the same as a cross-section of the catheter tube or infusion line.

9. A medical device according to claim 1, wherein the base element and the top element are made of watertight materials.

10. A medical device according to claim 1, wherein the base element comprises the slit and wherein the top element comprises the protrusion and/or wherein the second material is ethylene propylene diene monomer rubber.

11. A medical device according to claim 1, wherein the foil is transparent thus allowing visible inspection.

12. A medical device according to claim 1, wherein the foil is transparent and is configured to stick over the smooth upper surface.

13. A medical device according to claim 1, wherein the medical device comprises a guiding means for smoothly guiding the catheter tube or infusion line from an entry site at the skin to the base element of the medical device.

14. Use of a medical device according to claim 1 for liquid proof shielding of the catheter application area on a body of a living creature, the use comprising inserting the catheter tube or infusion line in the slit of the medical device and connecting the base element and the top element to each other.

15. Use of a medical device according to claim 1 for fixing the catheter tube or infusion line on a body of a living creature, the use comprising inserting the catheter tube or infusion line in the slit of the medical device and connecting the base element and the top element to each other.

* * * * *